United States Patent [19]

Strong

[11] Patent Number: 5,545,835
[45] Date of Patent: Aug. 13, 1996

[54] 5,6-DISUBSTITUTED-3-PYRIDYLMETHYL AMMONIUM HALIDE COMPOUNDS USEFUL FOR THE PREPARATION OF 5-(SUBSTITUTED METHYL)-2,3-PYRIDINEDICARBOXYLIC ACIDS

[75] Inventor: Henry L. Strong, Somerset, N.J.

[73] Assignee: American Cyanamid Company, Madison, N.J.

[21] Appl. No.: 334,297

[22] Filed: Nov. 4, 1994

Related U.S. Application Data

[62] Division of Ser. No. 156,205, Nov. 22, 1993, Pat. No. 5,378,843, which is a division of Ser. No. 960,749, Oct. 14, 1992, Pat. No. 5,288,866, which is a continuation-in-part of Ser. No. 812,520, Dec. 20, 1991, abandoned.

[51] Int. Cl.$^6$ ............ C07D 251/00; C07D 213/04; C07D 401/00
[52] U.S. Cl. ............ 544/215; 544/217; 544/218; 544/219; 544/234; 544/235; 544/236; 544/238; 544/244; 544/250; 544/275; 544/279; 544/280; 544/284; 544/298; 544/309; 544/333; 544/344; 544/345; 544/349; 544/350; 544/365; 546/250; 546/255; 546/261; 546/262; 546/114; 546/116; 546/113; 546/321; 546/147; 546/174
[58] Field of Search ............ 544/215, 217, 544/218, 219, 234, 235, 236, 238, 244, 250, 275, 279, 280, 284, 248, 309, 333, 344, 345, 349, 350, 365; 546/259, 255, 261, 262, 270, 271, 272, 273, 275, 276, 277, 278, 279, 289, 281

[56] References Cited

U.S. PATENT DOCUMENTS

| | | | |
|---|---|---|---|
| 4,748,244 | 5/1988 | Waldner et al. | 544/313 |
| 5,034,395 | 7/1991 | Tomado et al. | 546/275 |
| 5,063,237 | 11/1991 | Cooper et al. | 546/255 |
| 5,064,847 | 11/1991 | Archibald et al. | 546/277 |
| 5,125,961 | 6/1992 | Duinbouh et al. | 546/275 |
| 5,137,889 | 8/1992 | Tamado et al. | 544/365 |
| 5,262,384 | 11/1993 | Homprecht et al. | 504/225 |

FOREIGN PATENT DOCUMENTS

| | | |
|---|---|---|
| 0299362 | 1/1989 | European Pat. Off. . |
| 0461401 | 12/1991 | European Pat. Off. . |
| 2192877 | 1/1988 | United Kingdom . |

OTHER PUBLICATIONS

Chemical Abstracts. vol. 112, No. 0, Abstract No. 76.991a, Feb. 26, 1990.

*Primary Examiner*—C. Warren Ivy
*Assistant Examiner*—Raymond Covington
*Attorney, Agent, or Firm*—Peggy A. Climenson

[57] ABSTRACT

There are provided 5,6-disubstituted-3-pyridylmethyl ammonium halide compounds, a method for the preparation thereof and the use thereof for the preparation of 5-(substituted methyl)-2,3-pylidinedicarboxylic acids.

1 Claim, No Drawings

5,6-DISUBSTITUTED-3-PYRIDYLMETHYL AMMONIUM HALIDE COMPOUNDS USEFUL FOR THE PREPARATION OF 5-(SUBSTITUTED METHYL)-2,3-PYRIDINEDICARBOXYLIC ACIDS

This is a divisional of application Ser. No. 08/156,205 filed on Nov. 22, 1993, now U.S. Pat. No. 5,378,843, which is a divisional of application Ser. No. 07/960,749, filed on Oct. 14, 1992, which is now U.S. Pat. No. 5,288,866, which is a continuation-in-part of application Ser. No. 07/812,520 filed on Dec. 20, 1991, abandoned.

BACKGROUND OF THE INVENTION

Methods for the preparation of the 5-(and or 6)substituted 2-(2-imidazolin-2-yl)nicotinic acids, esters and salts involve the preparation of substituted-2,3-pyridinedicarboxylic acid anhydrides from substituted-2,3-pyridinedicarboxylic acids.

Methods for the preparation of 5-(substituted methyl)-2,3-pyridinedicarboxylic acids are rather limited and those methods that are available may require extensive purification methods to provide high purity 5-(substituted methyl)-2,3-pyridinedicarboxylic acids. For example, in Great Britain Patent No. 2,192,877 5-(substituted methyl)-2,3-pyridinedicarboxylic acids are prepared by halogenating 5-methyl-2,3-pyridinedicarboxylates to obtain 5-halomethyl-2,3-pyridinedicarboxylates. The 5-halomethyl-2,3-pyridinedicarboxylates are then reacted with a nucleophile and further reacted with aqueous alkali to obtain 5-(substituted methyl)-2,3-pyridinedicarboxylic acids. This method is not entirely satisfactory because the halogenation reaction produces a mixture that contains 5-halomethyl-2,3-pyridinedicarboxylates, 5-dihalomethyl-2,3-pyridinedicarboxylates and unreacted starting materials. Arduous or time-consuming purification methods are then needed to obtain high purity 5-halomethyl-2,3-pyridinedicarboxylates. If the mixture is not highly purified, the final herbicidal 5-(substituted methyl)-2-(2-imidazolin-2-yl)nicotinic acid, ester and salt compounds are contaminated with herbicidal compounds which have different herbicidal properties than the desired compounds.

Additionally, if the mixture is not highly purified, the nucleophile reacts with the 5-dihalomethyl-2,3-pyridinedicarboxylates to form undesirable 6-(and/or 4) substituted-5-(substituted methyl)-2,3-pyridinedicarboxylates. These undesirable compounds are difficult to separate from the desired 5-(substituted methyl)-2,3-pyridinedicarboxylates and contaminate the final herbicidal 5-(substituted methyl-2-(2-imidazolin-2-yl)nicotinic acid, ester and salt compounds.

It is, therefore, an object of this invention to provide high purity 5,6-disubstituted-3-pyridylmethyl ammonium halide compounds which are useful intermediates in the preparation of high purity 5-(substituted methyl)-2,3-pyridinedicarboxylic acids.

It is also an object of the invention to provide a method for the preparation of the 5,6-disubstituted-3-pyridylmethyl ammonium halide compounds and a method for the preparation of 5-(substituted methyl)-2,3-pyridinedicarboxylic acids from said 5,6-disubstituted-3-pyridylmethyl ammonium halide compounds.

SUMMARY OF THE INVENTION

The present invention relates to 5,6-disubstituted-3-pyridylmethyl ammonium halide compounds of formula I

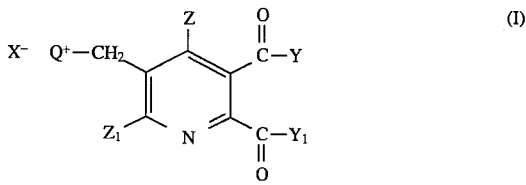

wherein
Z is hydrogen or halogen;
$Z_1$ is hydrogen, halogen, cyano or nitro;
X is Cl, Br, I or $R_3SO_3$;
$R_3$ is $C_1$–$C_4$ alkyl or phenyl optionally substituted with one to three $C_1$–$C_4$ alkoxy groups, $C_1$–$C_4$ alkyl groups, nitro groups, cyano groups or halogen atoms;
Y and $Y_1$ are each independently $OR_4$, $NR_4R_5$, or when taken together $YY_1$ is —O—, —S— or —$NR_6$—;
$R_4$ and $R_5$ are each independently hydrogen,
  $C_1$–$C_4$ alkyl optionally substituted with $C_1$–$C_4$ alkoxy or phenyl optionally substituted with one to three $C_1$–$C_4$ alkyl groups, $C_1$–$C_4$ alkoxy groups or halogen atoms, or
  phenyl optionally substituted with one to three $C_1$–$C_4$ alkyl groups, $C_1$–$C_4$ alkoxy groups or halogen atoms;
$R_6$ is hydrogen or $C_1$–$C_4$ alkyl;
Q is

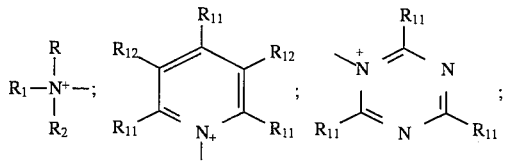

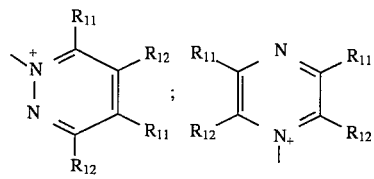

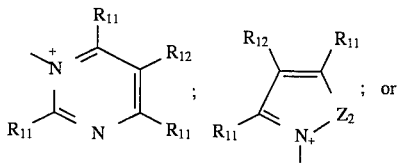

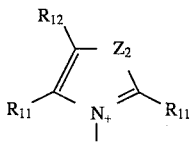

R, $R_1$ and $R_2$ are each independently $C_1$–$C_4$ alkyl, and when taken together, R and $R_1$ may form a 5- or 6-membered ring in which $RR_1$ is represented by the structure: —$(CH_2)_n$—, optionally interrupted by O, S or $NR_{10}$, where n is an integer of 3, 4 or 5, provided $R_2$ is $C_1$–$C_4$ alkyl;
$Z_2$ is O, S or $NR_{10}$;

$R_{10}$ is $C_1$–$C_4$ alkyl; and $R_{11}$ and $R_{12}$ are each independently hydrogen, halogen, $C_1$–$C_4$ alkyl or $C_1$–$C_4$ alkoxy, and when taken together, $R_{11}$ and $R_{12}$ may form a 5- or 6-membered saturated or unsaturated ring optionally interrupted by O, S, or $NR_{10}$ and optionally substituted with one to three halogen atoms, $C_1$–$C_4$ alkyl groups or $C_1$–$C_4$ alkoxy groups.

The present invention also relates to an efficient method for the preparation of high purity formula I compounds and their use in a method for the preparation of high purity 5-(substituted methyl)-2,3-pyridinedicarboxylic acid compounds of formula II

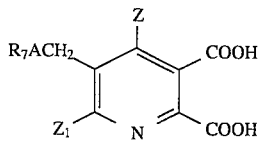

(II)

wherein

Z is hydrogen or halogen;

$Z_1$ is hydrogen, halogen, cyano or nitro;

A is O or S; and $R_7$ is $C_1$–$C_4$ alkyl optionally substituted with phenyl optionally substituted with one to three $C_1$–$C_4$ alkyl groups or halogen atoms, or phenyl optionally substituted with one to three $C_1$–$C_4$ alkyl groups or halogen atoms.

DETAILED DESCRIPTION OF THE INVENTION

Compounds of formula I, wherein X is Cl or Br, may be prepared by reacting 5-methyl-2,3-pyridine-dicarboxylic acid derivative compounds of formula III

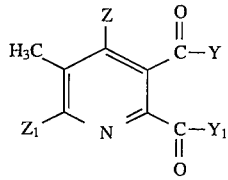

(III)

wherein Z, $Z_1$, Y and $Y_1$ are as described above with a halogenating agent in the presence of a first solvent, optionally in the presence of a catalytic amount of a radical initiator, preferably at a temperature range of about 0° C. to 100° C. to form a first mixture containing compounds of formula IV

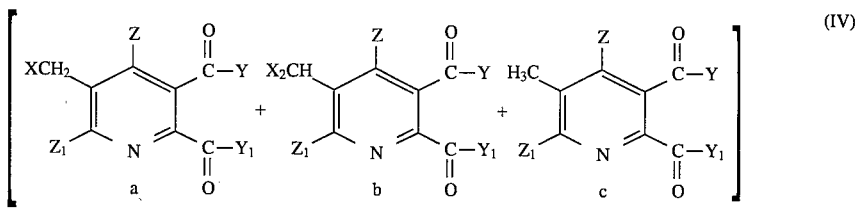

(IV)

wherein Z, $Z_1$, Y and $Y_1$ are as described above and X is Cl or Br. The amount of halogenating agent used is chosen to minimize the production of formula IVb compounds. Said first mixture is then reacted with at least 1.0 molar equivalent of a $C_1$–$C_4$ trialkylamine, a 5 to 6 membered saturated or 5 to 14 membered unsaturated heterocyclic amine optionally substituted with one to three $C_1$–$C_4$ alkyl groups, $C_1$–$C_4$ alkoxy groups or halogen atoms, in the presence of a second solvent preferably at a temperature range of about 0° C. to 100° C. to form 5,6-disubstituted-3-pyridylmethyl ammonium halide compounds of formula I. The method of preparation is illustrated in Flow Diagram I.

FLOW DIAGRAM I

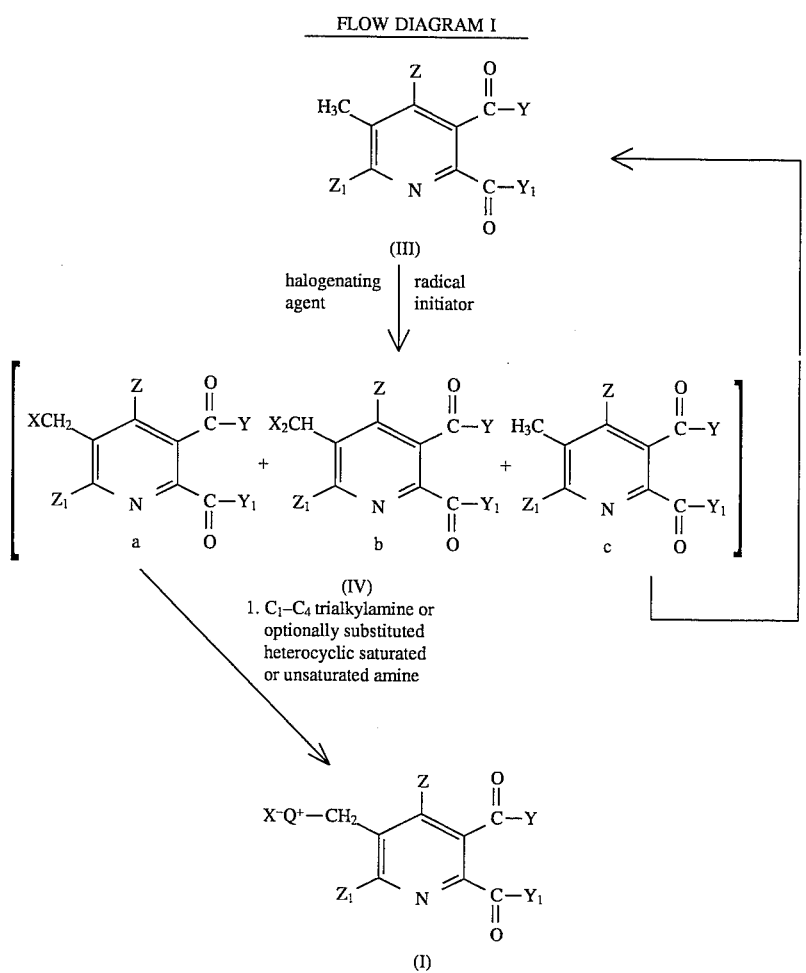

The above method is especially efficacious for the preparation of formula I compounds wherein Z is hydrogen;
$Z_1$ is hydrogen;
X is Cl or Br;
Y and $Y_1$ are each independently $OR_4$;
$R_4$ is $C_1$–$C_4$ alkyl; and
R, $R_1$ and $R_2$ are each independently methyl or ethyl, or when R and $R_1$ are taken together with the nitrogen atom to which they are attached they form a pyridine ring provided that $R_2$ is not present.

Preferred formula I compounds that are prepared by the method of the invention are [(5,6-dicarboxy-3-pyridyl)methyl]trimethylammonium bromide, dimethyl ester; [(5,6-dicarboxy-3-pyridyl)methyl]trimethylammonium bromide, diethyl ester; [(5,6-dicarboxy-3-pyridyl)methyl]pyridinium bromide, dimethyl ester; 1-[(5,6-dicarboxy-3-pyridyl)methyl]-4-methylpyridinium bromide, dimethyl ester; 1-[(5,6-dicarboxy-3-pyridyl)methyl]pyrazinium bromide, dimethyl ester; 1-[(5,6-dicarboxy-3-pyridyl)methyl]pyridazinium bromide, dimethyl ester; 1-[(5,6-dicarboxy-3-pyridyl) methyl]quinolinium bromide, dimethyl ester; 1-[(5,6-dicarboxy-3-pyridyl)methyl]isoquinolinium bromide, dimethyl ester; 3-[(5,6-dicarboxy-3-pyridyl)methyl]-4,5-dimethyl thiazolium bromide, dimethyl ester; 3-[(5,6-dicarboxy-3-pyridyl)methyl]-4-methylthiazolium bromide, dimethyl ester; and 1-[(5,6-dicarboxy-3-pyridyl)methyl]-3-methyl imidazolium bromide, dimethyl ester; and 1-[(5,6-dicarboxy-3-pyridyl)methyl]benzothiazolium bromide, dimethyl ester.

The formula I compounds may be isolated in high purity by filtration or, alternatively, by extraction with water.

The amines that may be used in the method of the invention are alkyl amines, 5 to 6 membered saturated and 5 to 14 membered unsaturated heterocyclic amines optionally substituted with one to three $C_1$–$C_4$ alkyl groups, $C_1$–$C_4$ alkoxy groups or halogen atoms. The preferred amines are $C_1$–$C_4$ trialkylamines, 5 or 6 membered saturated heterocyclic amines, and 5 to 14 membered unsaturated heterocyclic amines wherein the heterocyclic ring system contains one to three nitrogen atoms and optionally include sulfur or oxygen in the ring system.

The more preferred amines include the alkyl amines trimethyl amine and triethyl amine, the saturated heterocyclic amines including pyridines, picolines, pyrazines, pyridazines triazines, quinolines, isoquinolines, imidasoles, benzothiazoless and benzimidasoles, optionally substituted with one to three halogen atoms, $C_1$–$C_4$ alkyl groups or $C_1$–$C_4$ alkoxy groups, and unsaturated heterocyclic sines such as pyrrolidines, piperidines, piperazines, morpholines, thiazolidines and thiamorpholines.

The amount of halogenating agent used depends on both the reaction mode (batch vs. continuous) and the recycle procedures used to recover unreacted starting material. Typically a batch reaction will employ about 0.3 to 0.8 molar equivalents of the halogenating agent and in a continuous reaction, less molar equivalents of the halogenating agent are initially required.

Halogenating agents that may be used in the method of the invention include N-bromosuccinimide, 1,3-dibromo-5,5-dimethylhydantoin, bromine, chlorine, t-butylhypochlorite, sulfuryl chloride, sulfuryl bromide, N-chlorosuccinimide and the like. Preferred halogenating agents are chlorine, bromine, N-bromosuccinimide, 1,3-dibromo-5,5-dimethylhydantoin and sulfuryl chloride. Radical initiators suitable for use in the method of the invention include 2,2'-azobisisobutyronitrile, 2,2'-azobis(2-methylbutanenitrile), 2,2'-azobis(2,4-dimethylpentanenitrile), 1,1'-azobis(cyclohexanecarbonitrile), organic and inorganic peroxides such as hydrogen peroxide, benzoyl peroxide and the like, photochemical irradiation and the like with 2,2'-azobisisobutyronitrile and 2,2'-asobis(2-methylbutanenitrile) being preferred. Among the $C_1$–$C_4$ trialkylamines that may be used in the method of the invention are trimethylamine and triethylamine.

Solvents that may be used in the method of the invention include halogenated hydrocarbons such as dichloroethane, carbon tetrachloride and the like, halogenated aromatic hydrocarbons such as chlorobenzene, dichlorobenzene and the like, nitrobenzene, acetic acid, water, and alcohols such as methanol, ethanol, n-propanol and the like as well as mixtures of the above solvents. Preferred first solvents include chlorobenzene, dichlorobenzene and carbon tetrachloride and mixtures of chlorobenzene and methanol. Preferred second solvents include methanol, ethanol, chlorobenzene.

Suitable starting formula III compounds are described in U.S. Pat. Nos. 4,723,011, 4,748,244, European application No. 299-362-A and European application 292-032-A.

Another method of preparing certain formula I compounds is shown below in Flow Diagram II:

FLOW DIAGRAM II

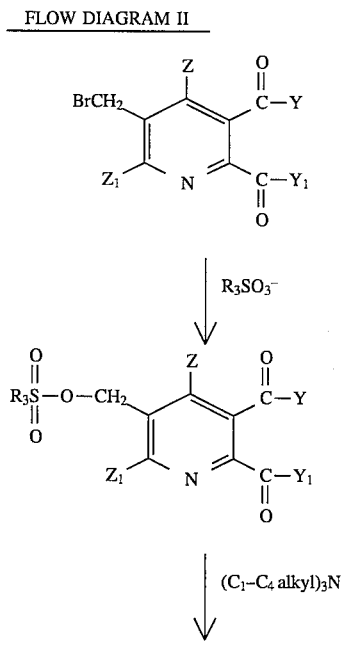

-continued
FLOW DIAGRAM II

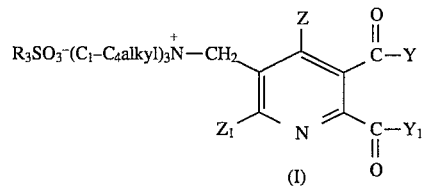

wherein Z, $Z_1$, $R_3$, Y and $Y_1$ are as described above for formula I.

Similarly, other formula I compounds may be prepared by the reaction scheme shown in Flow Diagram III:

FLOW DIAGRAM III

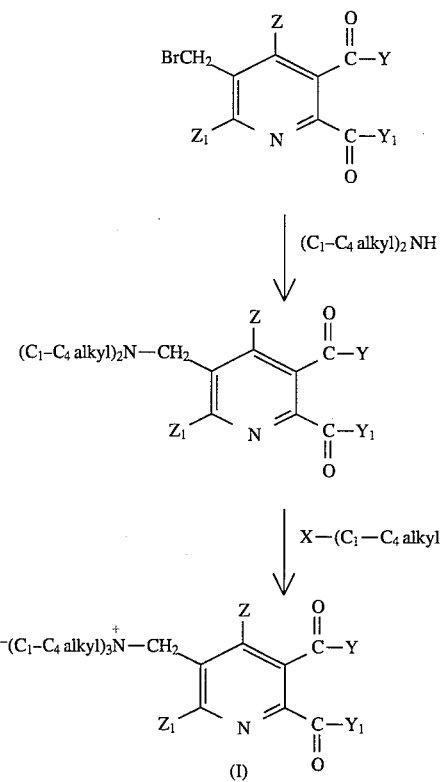

wherein Z, $Z_1$, Y and $Y_1$ are as described for formula I above and X is I or $R_3SO_3$ as described above.

Alternatively, compounds of formula I in which one of the R, $R_1$ or $R_2$ $C_1$–$C_4$ alkyl groups is attached to a polymeric material, may be prepared by passing the formula IV mixture over an anion exchange resin containing amine substituents. Advantageously, the formula IVb and IVc compounds do not react with the resin and are removed. The high purity ammonium halide compounds are further reacted to give formula II compounds.

The formula I compounds of the invention are intermediates in a method for the preparation of high purity 5-(substituted methyl)-2,3-pyridinedicarboxylic acid compounds of formula II. Compounds of formula II may be prepared by reacting 5,6-disubstituted-3-pyridylmethyl ammonium halide compounds of formula I as described above with at least 1.0 molar equivalent of an alkoxide or alkylsulfide compound of formula V $$R_7A^-M^+ \qquad\qquad (V)$$

wherein $R_7$ and A are as described above for formula II and M is an alkali metal such as sodium or potassium in the presence of an organic solvent preferably at a temperature range of 0° C. to 110° C. to form a first mixture further reacting said first mixture with at least 2.0 molar equivalents of an aqueous base preferably at a temperature range of about 20° C. to 120° C. to form a second mixture and adjusting the pH of said second mixture to a value below 2.5 with an acid to form 5-(substituted methyl)-2,3-pyridinedicarboxylic acid compounds of formula II. The method of preparation is illustrated in Flow Diagram IV.

FLOW DIAGRAM IV

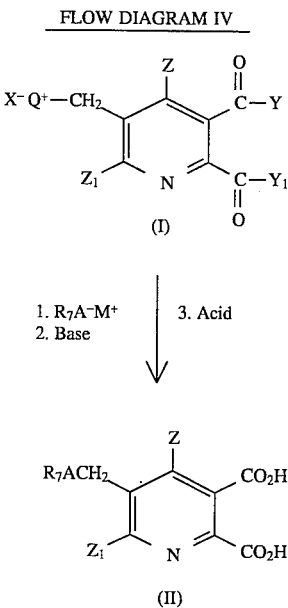

The above method of the invention is especially efficacious for the preparation of high purity formula II compounds wherein Z and $Z_1$ are hydrogen, A is O or S and $R_7$ is $C_1$–$C_4$ alkyl. A preferred formula II compound prepared by the method of the invention is 5-methoxymethyl-2,3-pyridinedicarboxylic acid.

The formula II compounds may be isolated by filtration or, alternatively, by extraction with a suitable solvent. In the isolation procedure suitable extraction solvents include tetrahydrofuran and water-immiscible alcohols alone or admixed with toluene.

Aqueous bases suitable for use in the method of the invention include aqueous sodium hydroxide solution, aqueous potassium hydroxide solution and the like. Acids that may be used in the method of the invention include mineral acids such as sulfuric acid, hydrochloric acid and the like.

Organic solvents that may be used in the method of the invention include acetonitrile, tetrahydrofuran, aromatic hydrocarbons, $R_7$OH alcohols wherein $R_7$ is as described above for formula II and the like. Preferred inert organic solvents include alcohols corresponding to $R_7$ in formula II above such as methanol and ethanol.

Alternatively, the corresponding diesters of formula II compounds may be prepared by the following reactions shown in Flow Diagram V:

FLOW DIAGRAM V

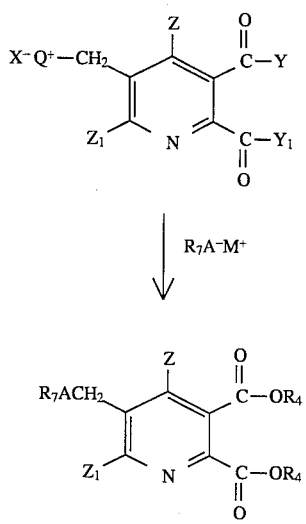

wherein Z, $Z_1$, $R_7$, A, Q, x and M are as described above and $R_4$ is $C_1$–$C_4$ alkyl optionally substituted with $C_1$–$C_4$ alkoxy or phenyl optionally substituted with one to three $C_1$–$C_4$ alkyl groups, $C_1$–$C_4$ alkoxy groups or halogen atoms, or phenyl optionally substituted with one to three $C_1$–$C_4$ alkyl groups, $C_1$–$C_4$ alkoxy groups or halogen atoms.

The high purity formula II compounds are useful as starting materials for the preparation of herbicidal 2-(2-imidasolin-2-yl)pyridine compounds having the structural formula VI

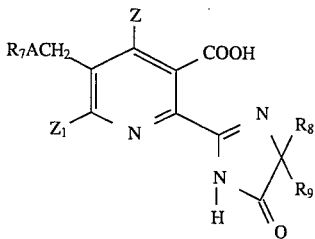

wherein
$R_8$ is $C_1$–$C_4$ alkyl;
$R_9$ is $C_1$–$C_4$ alkyl or $C_3$–$C_6$ cycloalkyl and when $R_8$ and $R_9$ are taken together with the carbon to which they are attached they may represent $C_3$–$C_6$ cycloalkyl optionally substituted with methyl;
Z is hydrogen or halogen;
$Z_1$ is hydrogen, halogen, cyano or nitro;
A is O or S;
$R_7$ is $C_1$–$C_4$ alkyl optionally substituted with phenol optionally substituted with one to three $C_1$–$C_4$ alkyl groups or halogen atoms, or phenol optionally substituted with one to three $C_1$–$C_4$ alkyl groups or halogen atoms; and when $R_8$ and $R_9$ represent different substituents, the optical isomers thereof.

Among the methods of preparation of the formula VI herbicidal compounds which utilize the corresponding formula II 2,3-pyridine carboxylic acids are those described in U.S. Pat. Nos. 4,460,776 and 4,798,619.

Advantageously, product formula VI compounds obtained from formula II compounds, prepared by the method of the invention, are surprisingly purer than formula VI compounds obtained by the methods of the prior art.

In order to facilitate a further understanding of the invention, the following examples are presented to illustrate more specific details thereof. The invention is not to be limited thereby except as defined in the claims. The term NMR designates nuclear magnetic resonance and the term HPLC designates high pressure liquid chromatography.

EXAMPLE 1

Preparation of
[(5,6-Dicarboxy-3-pyridyl)methyl]trimethylammonium bromide, dimethyl ester using N-bromosuccinimide

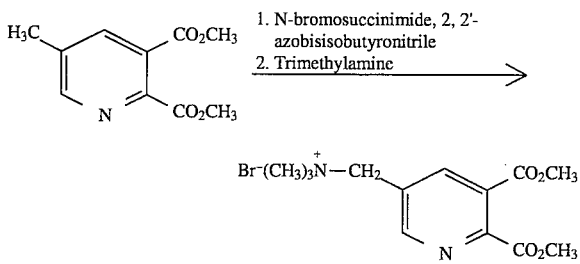

A mixture of dimethyl 5-methyl-2,3-pyridinedicarboxylate (523 g, 2.5 mol) in chlorobenzene (2,440 mL) is heated to 85° C. under nitrogen. A mixture of N-bromosuccinimide (356 g, 2.0 tool) and 2,2'-azobisisobutyronitrile (12.5 g, 0.076 mol) is added to the reaction mixture over 1 hour at 80°–90° C. After the addition is complete, the reaction mixture is held at 80° to 90° C. for 1 hour, cooled to room temperature overnight and diluted with water. The organic layer is separated, diluted with methanol, cooled to 10° C. and anhydrous trimethylamine (180 mL, 1.8 mol) is added. The reaction mixture is stirred at 5°–10° C. for 3 hours and filtered to obtain a solid. The solid is dried overnight in a vacuum oven to give the title product as a white solid (429 g, mp 200°–208° C. dec).

Following the above procedure, but substituting diethyl 5-methyl-2,3-pyridinedicarboxylate for dimethyl 5-methyl-2,3-pyridinedicdarboxylate gives [(5,6-dicarboxy-3-pyridyl)methyl]trimethylammonium bromide, diethyl ester as a white solid (mp 156°–161° C. dec).

EXAMPLE 2

Preparation of
[(5,6-Dicarboxy-3-pyridyl)methyl]trimethylammonium bromide, dimethyl ester using
1,3-dibromo-5,5-dimethylhydantoin

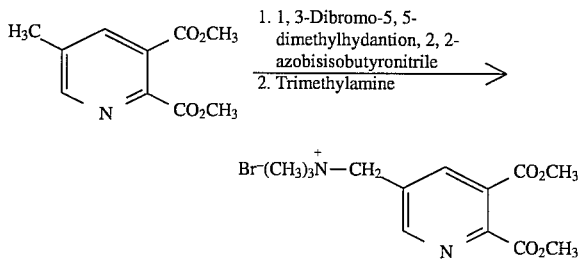

A mixture of dimethyl 5-methyl-2,3-pyridinedicarboxylate (104.5 g, 0.5 mol) in chlorobenzene (470 mL) is heated to 85° C. under nitrogen. A mixture of 1,3-dibromo-5,5-dimethylhydantoin (71.5 g, 0.25 mol) and 2,2'-azobisisobutyronitrile (2.5 g, 0.015 mol) is added to the reaction mixture over 30 minutes at 80°–95° C. After the addition is complete, the reaction mixture is held at 80° to 85° C. for 3.5 hours, cooled to room temperature, washed with water and dried. The dried organic mixture is diluted with methanol, cooled to 10° C. and anhydrous trimethylamine (17.4 g, 0.29 mol) is added. The reaction mixture is stirred at 10°–36° C. overnight and filtered to obtain a solid. The solid is washed with chlorobensene and vacuum dried to give the title product as a white solid (74.4 g, mp 200°–208° C. dec).

EXAMPLE 3

Preparation of
5-(Methoxymethyl)-2,3-pyridinedicarboxylic acid

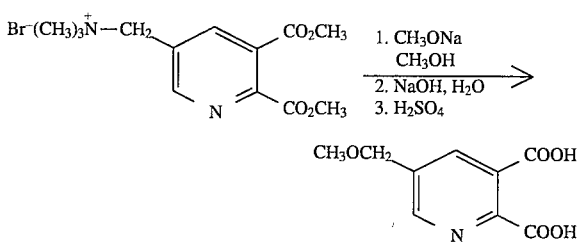

A mixture of 25% sodium methoxide in methanol (270 g, 1.25 mol) and [(5,6-dicarboxy-3-pyridyl)-methyl]trimethylammonium bromide, dimethyl ester (347 g, 1.00 mol) in methanol (650 mL) is heated at reflux for I hour under nitrogen. Water (1 L) and sodium hydroxide (80.0 g, 2.0 mol) are added and the reaction mixture is distilled until the pot is 100°–105° C. The reaction mixture is cooled to room temperature, treated with sulfuric acid to adjust the pH to a value from 1.5 to 2 and filtered to obtain a solid. The solid is washed with water and dried in a vacuum oven to obtain the title product as a white solid (mp 161°–162° C.) which is greater than 99% pure by HPLC analysis.

EXAMPLE 4

Preparation of Dimethyl
5-(bromomethyl)-2,3-pyridine-dicarboxylate

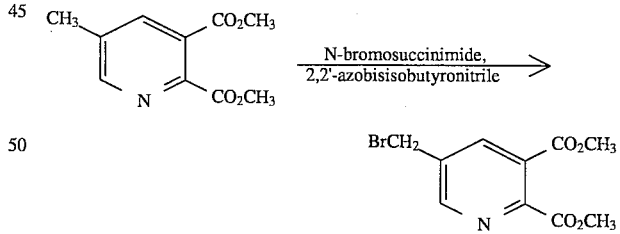

A mixture of dimethyl 5-methyl-2,3-pyridinedicarboxylate (30.0 g, 0.143 mol), N-bromosuccinimide (32.0 g, 0.18 mol) and 2,2'-azobisisobutyronitrile (0.9 g, 0.0055 mol) in carbon tetrachloride (200 mL) is heated at 80° C. for 1.5 hours. Additional 2,2'-azobisisobutyronitrile (0.9 g, 0.0055 mol) is added and the reaction mixture is heated at reflux for 2 hours, cooled to room temperature and filtered. The filter cake is washed with carbon tetrachloride. The filtrate and wash are combined, washed with water and concentrated in vacuo to give an oil. The oil is shown by HPLC to contain 57% of the title product, 16% dimethyl 5-methyl-2,3-pyridinedicarboxylate and 23% dimethyl 5-dibromomethyl-2,3-pyridinedicarboxylate.

EXAMPLE 5

Preparation of
[(5,6-Dicarboxy-3-pyridyl)methyl]pyridiniumbromide,
dimethyl ester

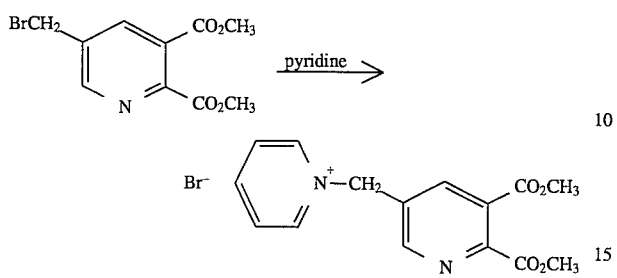

A mixture of the oil prepared in example 6 (32.0 g) and pyridine (9.2 g, 0.12 mol) in absolute ethanol is heated at reflux for 2 hours under nitrogen, cooled to room temperature and filtered. The filter cake is washed with ethanol and vacuum dried at 50° C. to give the title product as a solid (18.1 g) which is greater than 99% pure by HPLC analysis.

EXAMPLE 6

Preparation of [(5,6-Dicarboxy-3-pyridyl(methyl]
trimethylammonium bromide, dimethyl ester in
ethanol using anhydrous trimethylamine

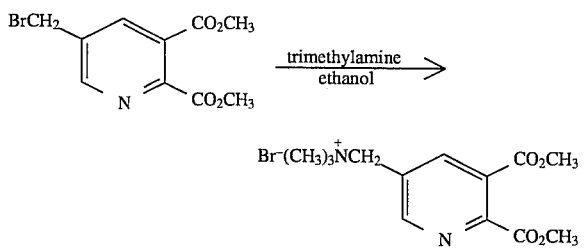

A mixture of an oil prepared according to the procedure of example 6 (100 g) in absolute ethanol is cooled to 5° C. under nitrogen. Anhydrous trimethylamine (16 g, 0.27 mol) is added and the reaction mixture is stirred for 3 hours at 5° C. and filtered. The filter cake is washed with ethanol and air dried to give the title product as a white solid (49.1 g).

EXAMPLE 7

Preparation of Dimethyl
5-(methoxymethyl)-2,3-pyridinedicarboxylate

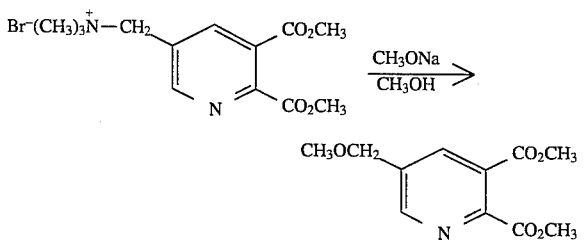

A mixture of 25% sodium methoxide in methanol (320.0 g, 1.5 mol) and [(5,6-dicarboxy-3-pyridyl)methyl]trimethylammonium bromide, dimethyl ester (160.0 g, 0.5 mol) in methanol (650 mL) is heated at reflux for 6 hours under nitrogen. The reaction mixture is cooled to 5° C. and acetic acid (90 g) and water (200 mL) are added. Methanol is removed in vacuo, water is added and the mixture is extracted with methylene chloride. The combined organic extracts are washed sequentially with 5% sodium bicarbonate solution and water and concentrated in vacuo to obtain the title product as a clear liquid (83.2 g) which is identified by $^1$H NMR spectral analysis.

Following the above procedure, but substituting [(5,6-dicarboxy-3-pyridyl)methyl]pyridinium bromide, dimethyl ester for [(5,6-dicarboxy-3-pyridyl)methyl]trimethylammonium bromide, dimethyl ester gives the title product as a clear liquid.

EXAMPLE 8

Preparation of
5-(Methoxymethyl)-2,3-pyridinedicarboxylic acid

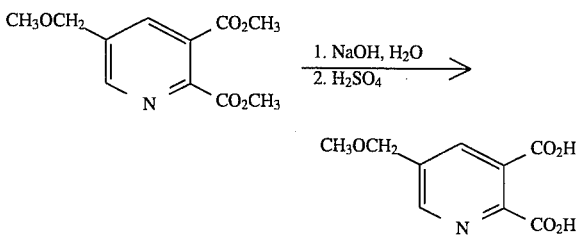

A mixture of dimethyl 5-(methoxymethyl)-2,3-pyridinedicarboxylate (60.0 g, 0.25 mol) and 50% sodium hydroxide solution (50.0 g, 0.63 mol) in water is heated at 90°–110° C. for 2 hours under nitrogen while distilling off methanol and water. The reaction mixture is cooled to 10° C., treated with sulfuric acid to adjust the pH to 2.0 and filtered to obtain a solid. The solid is washed with water and vacuum dried to give the title product as a white solid (44.3 g, mp 161°–162° C.).

EXAMPLE 9

Preparation of 2,3-pyridinedicarboxylic acid,
5-(aromatic amine) methyl bromide, dimethyl ester

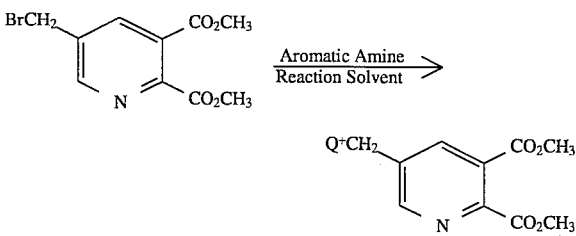

To a 250 mL flask under nitrogen were added the reaction solvent set forth in Table I (either 100 mL g of absolute ethanol or 200 mL of a 50/50 mixture of methanol/chlorobenzene), and 30 g of crude 5-monobromomethyl pyridine-2,3-dicarboxylic acid, dimethyl ester (57% real by HPLC), and 0.1 moles of an aromatic amine set forth in Table I. The mixture was heated to reflux and held for approximately 5 hours. The reaction solvent was removed under vacuum at 40°–60° C. The resulting residue was cooled to room temperature and slurried with approximately 100 mL of an organic solvent identified as the "Slurry Solvent" in Table I. The mixture was then filtered and the cake was washed with approximately 50 mL of the slurry solvent. The resulting crystalline solid was vacuum dried at 50° C. The melting points were then taken and structure was confirmed by $^1$H, $^{13}$C, NMR and $^{13}$C ATP1 NMR.

TABLE I

AROMATIC AMINE SALTS OF 5-METHYL-2,3-DICARBOXYLIC DIMETHYL ESTER

| Q+ | Aromatic Amine | Reaction Solvent | Slurry Solvent | Isolated Salt Yield, g | Melting Point °C. |
|---|---|---|---|---|---|
| 4-picolinium | 4-Picoline | Ethanol | Acetone | 15.2 | 155–157 |
| pyrazinium | Pyrazine | Ethanol | Ethanol | 12.5 | 167–169 |
| pyridazinium | Pyridazine | Ethanol | Acetone | 18.2 | 135–137 |
| quinolinium | Quinoline | Ethanol | Acetone/Toluene | 14.6 | 112–114 |
| isoquinolinium | Isoquinoline | Methanol/Chlorobenzene | Acetone | 22.9 | 164–166 |
| 4,5-dimethylthiazolium | 4,5-dimethylthiazole | Ethanol | THF | 9.2 | 133–140 |
| 4-methylthiazolium | 4-Methylthiazole | Ethanol | THF | 9.0 | 112–115 |
| 1-methylimidazolium | 1-Methylimidazole | Methanol/Chlorobenzene | Acetone | 19.4 | 109–111 |
| benzothiazolium | Benzothiazole | Ethanol | Acetone | 6.4 | 93–97 |

I claim:

1. A 5,6-disubstituted-3-pyridylmethylammonium halide compound having the structural formula

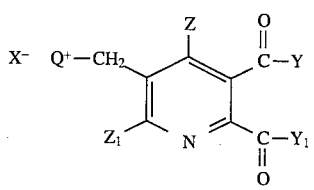

(I)

wherein

Z is hydrogen or halogen;

$Z_1$ is hydrogen, halogen, cyano or nitro;

X is Cl, Br, I or $R_3SO_3$;

$R_3$ is $C_1$–$C_4$ alkyl or
phenyl optionally substituted with one to three $C_1$–$C_4$ alkoxy groups, $C_1$–$C_4$ alkyl groups, nitro groups, cyano groups or halogen atoms;

Y and $Y_1$ are taken together form a group YY which is —O—, —S— or —$NR_6$—;

$R_4$ and $R_5$ are each independently hydrogen,
$C_1$–$C_4$ alkyl optionally substituted with $C_1$–$C_4$ alkoxy or phenyl optionally substituted with one to three $C_1$–$C_4$ alkyl groups, $C_1$–$C_4$ alkoxy groups or halogen atoms, or
phenyl optionally substituted with one to three $C_1$–$C_4$ alkyl groups, $C_1$–$C_4$ alkoxy groups or halogen atoms;

$R_6$ is hydrogen or $C_1$–$C_4$ alkyl;

Q is

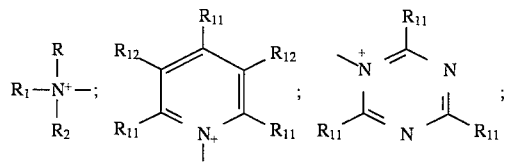

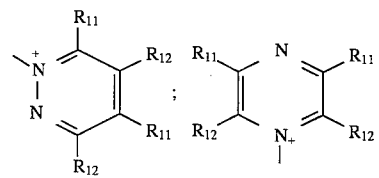

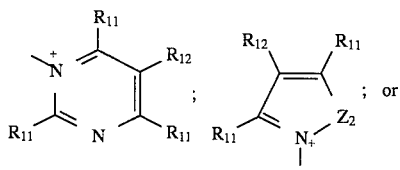

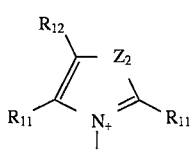

R, $R_1$ and $R_2$ are each independently $C_1$–$C_4$ alkyl, and when taken together, R and $R_1$ may form a 5- or 6-membered ring in which $RR_1$ is represented by the structure: —$(CH_2)_n$—, optionally interrupted by O, S or $NR_{10}$, where n is an integer of 3, 4 or 5, provided $R_2$ is $C_1$–$C_4$ alkyl;

$Z_2$ is O, S or $NR_{10}$;

$R_{10}$ is $C_1$–$C_4$ alkyl; and $R_{11}$ and $R_{12}$ are each independently hydrogen, halogen, $C_1$–$C_4$ alkyl or $C_1$–$C_4$ alkoxy, and when taken together, $R_{11}$ and $R_{12}$ may form a 5- or 6-membered saturated or unsaturated ring optionally interrupted by O, S, or $NR_{10}$ and optionally substituted with one to three halogen atoms, $C_1$–$C_4$ alkyl groups or $C_1$–$C_4$ alkoxy groups.

* * * * *